(12) United States Patent
Rigby et al.

(10) Patent No.: US 8,375,766 B2
(45) Date of Patent: Feb. 19, 2013

(54) METHODS AND APPARATUS FOR MONITORING PARTICLES FLOWING IN A STACK

(75) Inventors: Michael Rigby, Ramsey (GB); William John Averdieck, Nr. Haverhill (GB)

(73) Assignee: PCME Limited (GB)

( * ) Notice: Subject to any disclaimer, the term of this patent is extended or adjusted under 35 U.S.C. 154(b) by 731 days.

(21) Appl. No.: 12/520,217

(22) PCT Filed: Dec. 19, 2007

(86) PCT No.: PCT/GB2007/004887
§ 371 (c)(1),
(2), (4) Date: Nov. 25, 2009

(87) PCT Pub. No.: WO2008/075046
PCT Pub. Date: Jun. 26, 2008

(65) Prior Publication Data
US 2010/0101300 A1 Apr. 29, 2010

(30) Foreign Application Priority Data
Dec. 19, 2006 (GB) .................................. 0625326.4

(51) Int. Cl.
*G01N 21/00* (2006.01)
(52) U.S. Cl. .......................................... 73/1.06; 356/338
(58) Field of Classification Search .................... 73/1.06; 356/335–344
See application file for complete search history.

(56) References Cited

U.S. PATENT DOCUMENTS

| | | | |
|---|---|---|---|
| 5,591,895 A | 1/1997 | Rigby | |
| 6,965,240 B1 | 11/2005 | Litton et al. | |
| 8,134,706 B2 * | 3/2012 | Rogers et al. | 356/338 |
| 2005/0005677 A1 | 1/2005 | Smith | |

FOREIGN PATENT DOCUMENTS

| | | |
|---|---|---|
| EP | 1251344 A | 10/2002 |
| GB | 2266772 A | 11/1993 |
| GB | 2390893 A | 1/2004 |
| GB | 2422897 A | 8/2006 |
| WO | 94/03792 A | 2/1994 |

OTHER PUBLICATIONS

International Search Report for PCT/GB2007/004887 dated Mar. 31, 2008.
UK Search Report GB0625326.4; May 4, 2007.

* cited by examiner

*Primary Examiner* — Hezron E Williams
*Assistant Examiner* — Rodney T Frank
(74) *Attorney, Agent, or Firm* — Kramer Levin Naftalis & Frankel LLP

(57) ABSTRACT

An apparatus (7) for monitoring particles flowing in a stack (6), comprises: an electrical-interaction monitor (1) operable to provide a signal (300) resulting from electrical interaction of the particles with the monitor (1). a scattered-light monitor (10) operable to provide a signal (310) resulting from detection of light scattered from the particles, and a controller (320) arranged to alter the calibration of the electrical-interaction monitor 1 in response to changes in the relative magnitude of the electrical-interaction (signal 300) and the scattered-light signal (310).

2 Claims, 6 Drawing Sheets

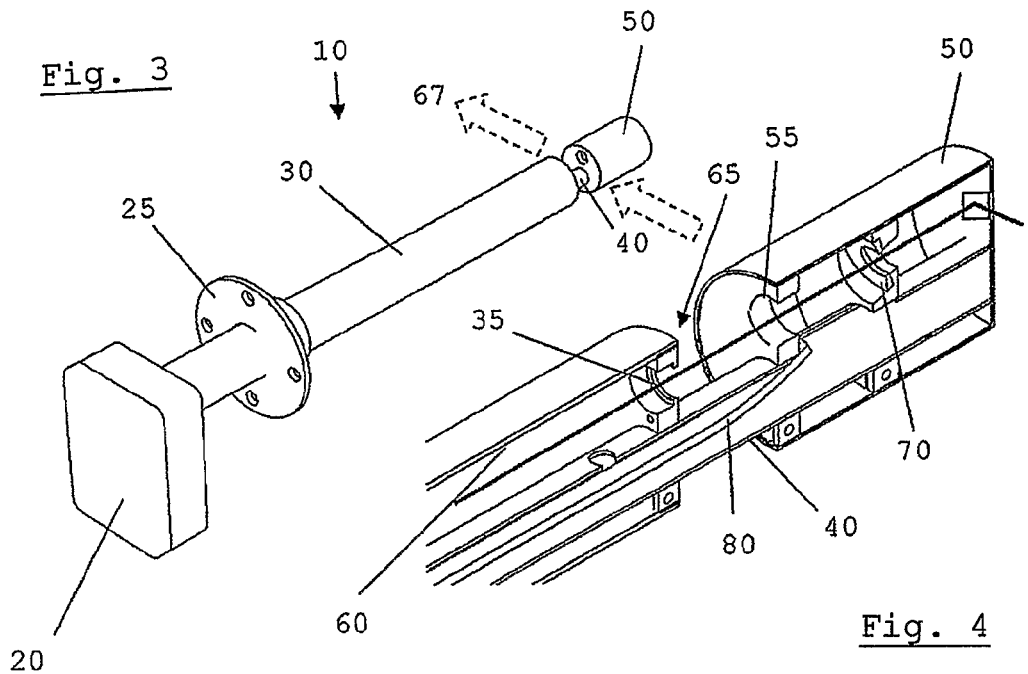
Fig. 3
Fig. 4
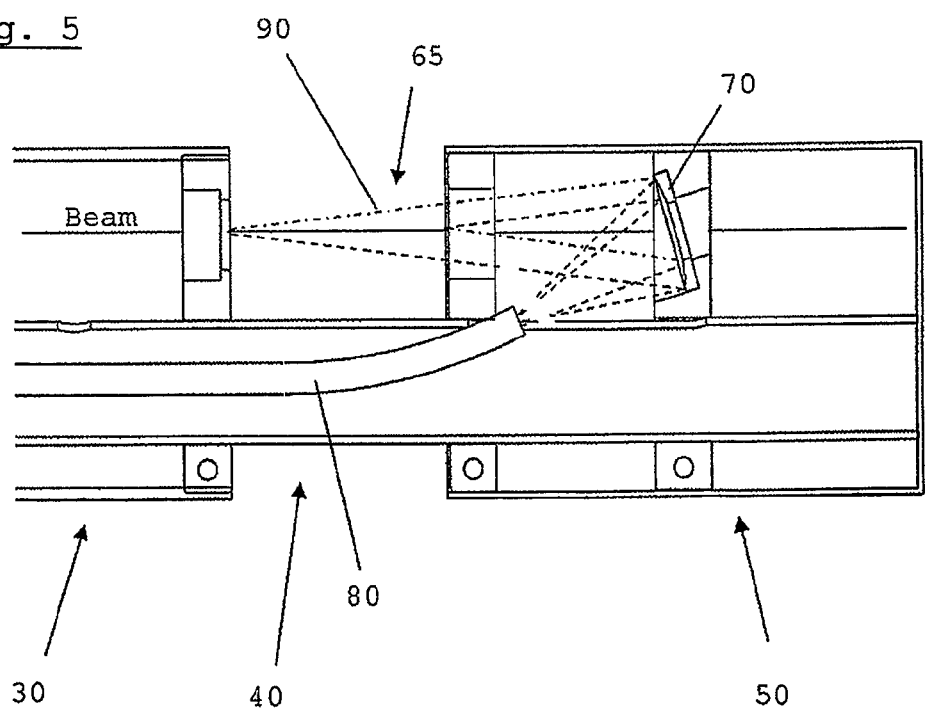
Fig. 5

Fig. 8
(a)
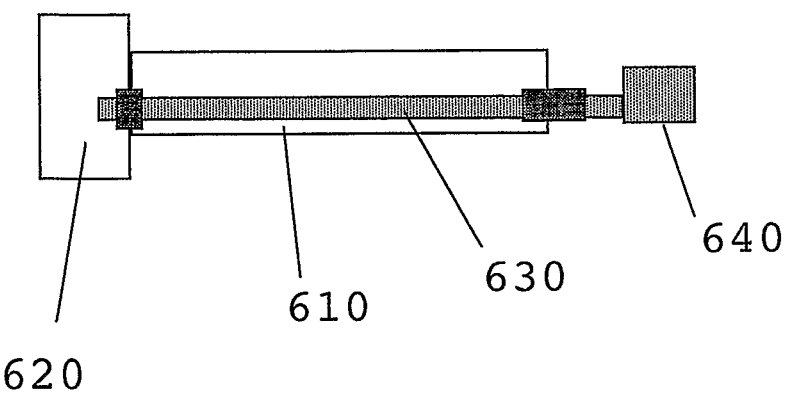
620  610  630  640
(b)
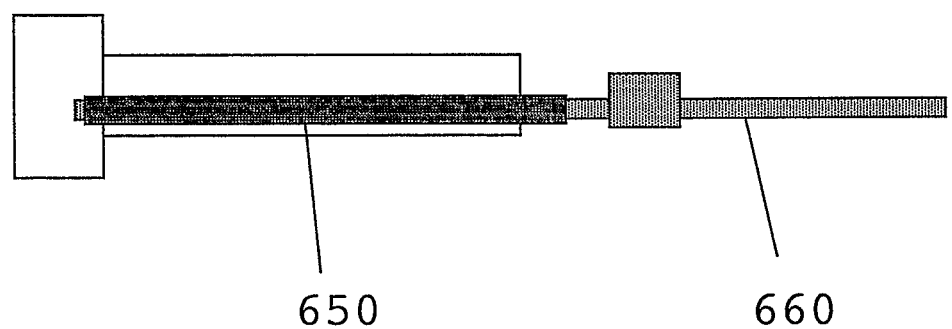
650  660

METHODS AND APPARATUS FOR MONITORING PARTICLES FLOWING IN A STACK

This application is the United States national stage filing of corresponding international application number PCT/GB2007/004887 filed Dec. 19, 2007, which claims priority to Great Britain patent application No. 0625326.4, filed Dec. 19, 2006, all of which are hereby incorporated by reference in their entirety.

FIELD OF THE INVENTION

This invention relates to monitoring particles flowing in a stack. More particularly, although not exclusively, the present invention relates to calibration of apparatus for monitoring such particle flows. Even more particularly, although not exclusively, the present invention relates to independent auditing of the calibration of such apparatus.

BACKGROUND ART

Particulates emitted from industrial stacks are monitored for a number of reasons. Several countries impose regulatory restrictions on emissions, and monitoring is necessary to ensure compliance. Increasingly, companies have their own internal environmental programs and monitor emissions to provide data for those, and for their internal quality control procedures. Companies also monitor emissions in order to improve their own processes, for example by improving powder production, reducing product loss from process-particle collection devices and reducing running costs of fabric filters (by extending bag life).

Several different techniques have been used for monitoring emissions from industrial stacks, and more particularly for measuring particle flow in stacks. Two important techniques are those using electrodynamic instruments and those using forward-scatter monitors.

Electrodynamic instruments measure an ac current resulting from particles interacting with a probe rod that projects into the stack. These instruments give reliable long-term operation, have high resolution (of value in analysis of bag-filter emission dynamics), have no moving parts, and provide a representative measurement over the length of the rod (which is typically up to 1 m in length). Their major shortcomings are that calibration can drift over time, particularly if the average charge on the flowing particles changes, and that it is difficult to audit the technique with a surrogate (we know of no good surrogate for dust which accurately simulates dust interaction with the rod). The key application area for this technique has been in monitoring stacks associated with bag-filters, where the charge on the particles tends to remain relatively constant.

Forward-scatter monitors measure the intensity of a light scattered by particles in a forward direction from an incident laser beam or other light beam. These instruments provide a high-accuracy measurement, which can be audited with surrogate scattering bodies (for example, a glass slide with an opal surface). Their major shortcomings are that the measurement volume is relatively small and that it is difficult to keep optical surfaces clean (which can cause drift in the measurement) even using sophisticated air purges.

The present invention seeks to ameliorate at least some of the abovementioned problems.

DISCLOSURE OF THE INVENTION

In a first aspect, the invention provides an apparatus for monitoring particles flowing in a stack, comprising:

(1) an electrical-interaction monitor operable to provide a signal resulting from electrical interaction of the particles with the monitor, the monitor having a first calibration;

(2) a scattered-light monitor operable to provide a signal resulting from detection of light scattered from the particles;

(3) a controller arranged to alter the calibration of the electrical-interaction monitor in response to changes in the relative magnitude of the electrical-interaction signal and the scattered-light signal.

The apparatus thus combines electrodynamic and light scatter technology in the same instrument to obtain better overall performance than the techniques provide when used separately. The robust, high resolution and representative performance of the electrodynamic measurement is enhanced by the more stable accuracy and auditability characteristics of light scatter.

The electrodynamic signal is referenced periodically against the more stable scattered-light signal, reducing the need for costly calibrations of the electrical-interaction monitor with a gravimetric sample. The apparatus may thus be used in applications where electrodynamic instruments cannot normally be used, for example processes from which particulate is controlled with Electrostatic Precipitator abatement equipment (common in the power industry) and varying velocity applications (in both of those applications, the charge on the flowing particles can change with time, making prior-art electrodynamic instruments not sufficiently accurate).

The instrument need only make light-scatter measurements intermittently, which means that its optical components need only be exposed to dust for short durations, hence reducing the need for costly air purges and window cleaning, and increasing the reliability of the instrument.

Also, in electrodynamic mode, the instrument has a much larger measurement volume than a light-scatter detector, thus providing a more representative measurement of stack emissions, as well as more robust operation and higher resolution.

The electrical-interaction monitor may comprise a rod comprising a mount for mounting the rod in or on a wall of the stack so that the rod projects into the stack.

The electrical-interaction monitor may comprise a ring for mounting around the inside of a wall of the stack.

The electrical-interaction monitor may include a covering of insulation. The insulation may extend across all of the monitor's surface area that is exposed to particle flow.

The electrical interaction of flowing particles with monitors is generally believed to result from triboelectric interactions between the particles and the monitor. However, the nature of the interaction is not fully understood by persons skilled in the art.

The electrical-interaction signal may be an alternating-current (AC) signal. The apparatus may include a high-pass filter to eliminate direct-current (DC) components of the signal. The electrical-interaction signal may be a direct-current (DC) signal. The apparatus may include a low-pass filter to separate the DC signal from AC components of the signal.

The scattered-light monitor may comprise a light transmitter on a first side of a scattering zone and a scattered-light receiver on a second, opposite, side of said scattering zone, the transmitter and receiver being arranged so that light passes from the transmitter and into the scattering zone, with light scattered from the scattering zone being received by the receiver. The light transmitter may comprise a laser. The light receiver may comprise a photodiode.

The transmitter and receiver may be mounted at opposing locations in, on or adjacent to the wall of the stack.

Preferably, the transmitter and receiver are mounted outside the particle flow; that reduces the risk of damage to those elements of the monitor by hot gases and/or particles. Therefore, the scattered-light monitor may include a rod, mounted in the wall of the stack at the rod's proximal end and a reflector at the rod's distal end. The rod may include a waveguide, for example an optical fibre, arranged to guide scattered light from the reflector to the receiver. The transmitter and receiver may then be mounted on the same side of the stack. The rod may project into the particle flow, so that flowing particles pass through the scattering zone.

The controller may include a microprocessor.

Instruments according to embodiments of the invention may be especially advantageous as replacements for triboelectric instruments which drift due to contamination In a second aspect, the invention provides a method of monitoring particles flowing in a stack, comprising:

(1) monitoring a signal resulting from electrical interaction of the particles with an electrical-interaction monitor having a first calibration;

(2) calculating from the monitored electrical-interaction signal, according to the first calibration, a value for a parameter relating to the particle flow;

(2) monitoring a signal resulting from detection of light scattered from the particles;

(3) comparing the electrical-interaction signal with the scattered-light signal to obtain a relative magnitude of the signals;

(4) identifying a change in the relative magnitude of the signals;

(5) altering the calibration of the electrical-interaction monitor in response to the change;

(6) calculating from the monitored electrical-interaction signal, according to the altered calibration, an altered value for the parameter relating to the particle flow.

The scattered-light signal may be monitored intermittently. The scattered-light signal may be monitored at regular intervals, for example once every day. The electrical-interaction signal may be monitored continuously, whilst the apparatus is in use.

The signals may be compared by calculating the ratio of the electrical-interaction signal to the scattered-light signal, and changes in that ratio identified.

In a third aspect, the invention provides a method of monitoring particles flowing in a stack, comprising:

(1) providing an electrical-interaction monitor operable to provide a signal resulting from electrical interaction of the particles with the monitor, the monitor having a first calibration;

(2) providing a scattered-light monitor operable to provide a signal resulting from detection of light scattered from the particles, the monitor having a first calibration;

(3) monitoring with the scattered-light monitor a signal resulting from detection of light scattered from a particulate surrogate material;

(4) recalibrating the scattered-light monitor in response to changes in the monitored scattered-light signal.

(5) recalibrating the electrical-interaction monitor in response to changes in the calibration of the scattered-light monitor;

(6) monitoring a signal resulting from electrical interaction of the flowing particles with the recalibrated monitor.

In a fourth aspect, the invention provides an apparatus for monitoring particles flowing in a stack, comprising:

(1) an electrical-interaction monitor operable to provide a signal resulting from electrical interaction of the particles with the monitor, the monitor having a first calibration;

(2) a scattered-light monitor operable to provide a signal resulting from detection of light scattered from the particles;

(3) a controller arranged to alter the calibration of the electrical-interaction monitor in response to changes in the calibration of the scattered-light monitor.

As the electrodynamic monitor can be related to the light scattering response, the auditing of the scattering response provides a derived audit for the electrodynamic response. With current regulations (such as EN-14181 in Europe) putting increased importance on independent auditing of the correct operation of the emission monitor this feature is especially advantageous.

It will be appreciated that features of the present invention described above in relation to the first, second, third or fourth aspect of the present invention are equally applicable to any other of the first, second, third or fourth aspects of the present invention; for example, features of the present invention described in relation to an apparatus of the present invention are equally applicable to a method of the present invention, and vice versa.

BRIEF DESCRIPTION OF THE DRAWINGS

Certain illustrative embodiments of the invention will now be described in detail, by way of example only, with reference to the accompanying schematic drawings, in which:

FIG. 3 is a perspective view of the light-scattering monitor of the apparatus of FIG. 1 instrument according to the invention;

FIG. 4 is a cut-away view of part of a proximal portion, a medial portion and a distal portion of the instrument of FIG. 3;

FIG. 5 is a cross-sectional view corresponding to FIG. 4, showing scattering of light between the proximal housing portion and the distal housing portion;

FIGS. 8 (*a*) and (*b*) are two further example embodiments of the invention.

DETAILED DESCRIPTION

Figure 1:
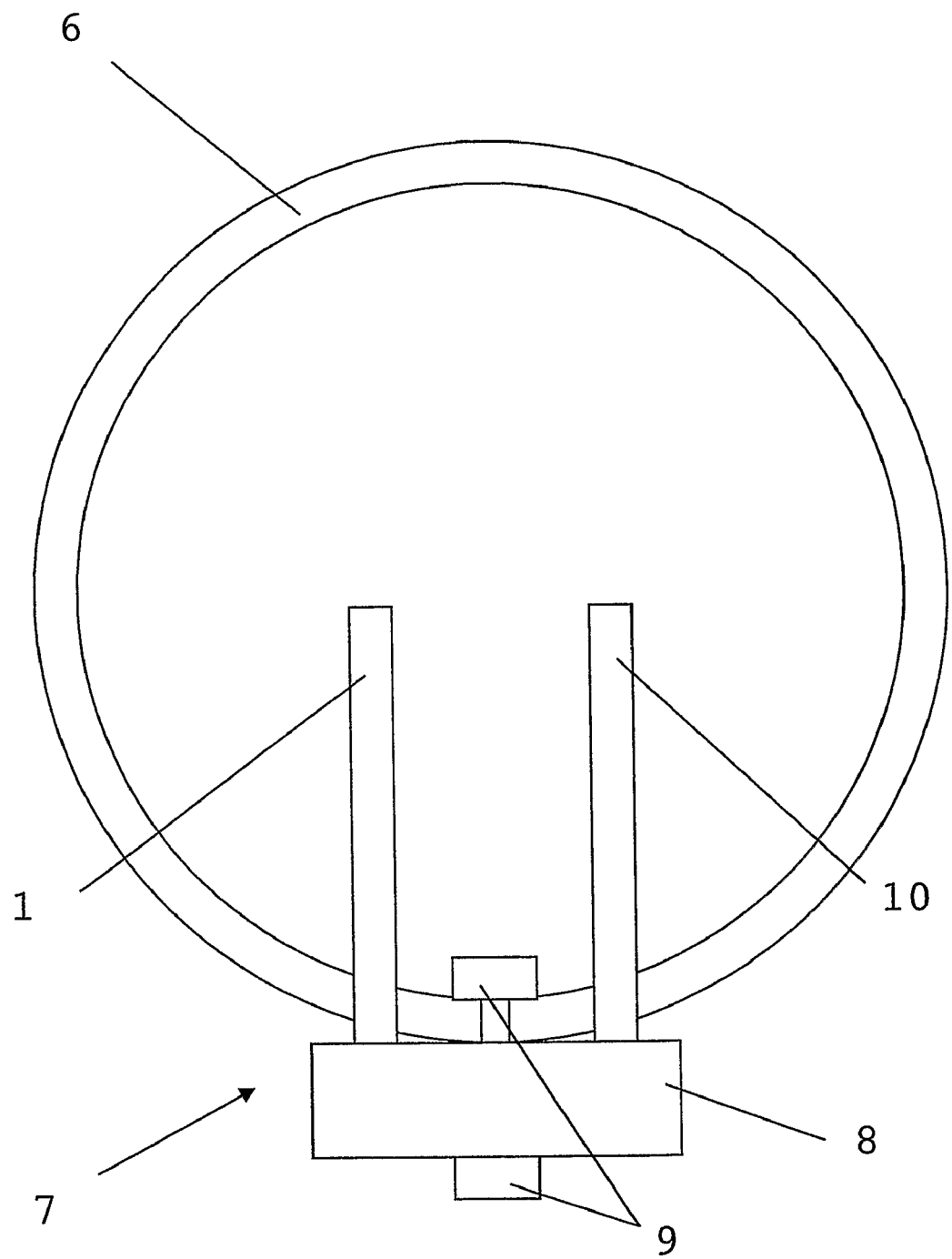
FIG. 1 is a schematic plan view of an apparatus according to an example embodiment of the invention mounted in the wall of a stack in which particles flow.

In FIG. 1, an example particle monitoring apparatus 7 according to an embodiment of the invention is shown mounted in the wall of a stack 6. Apparatus body 8 is mounted outside the stack 6 by mounting means 9. Two probes 1, 10 project from the body 8 through the wall into the interior of stack 6.

The first probe 1 is a rod for measuring electrical signals arising from interactions between particles flowing in stack 6. The second probe 10 is for measuring light scattering from the particles.

The apparatus can operate in 3 modes:

(1) Electrodynamic running mode: this is the most common mode of operation in which the electrodynamic signal is measured and the dust concentration is derived by multiplying this signal by a predetermined calibration factor. In this mode the light scatter detector is not operational and all optics are protected from the process gas and dust.

(2) Referencing mode: in which the electrodynamic signal and light scatter signal are periodically measured in parallel for a short duration (in this example, 1 to 5 minutes) and a ratio of scattered signal to electrodynamic signal is measured. The electrodynamic calibration factor is subsequently adjusted for any change in this ratio which is assumed to come from drift in the electrodynamic signal.

(3) Auditing mode: in which the instrument is operated in light scatter mode so that a reference scattering body may be automatically (or manually) inserted in the measurement volume to check for any change in scattering response. A change in response can be used to compensate for long term instrument drift or simply to check ongoing correct operation of the instrument.

Figure 2:
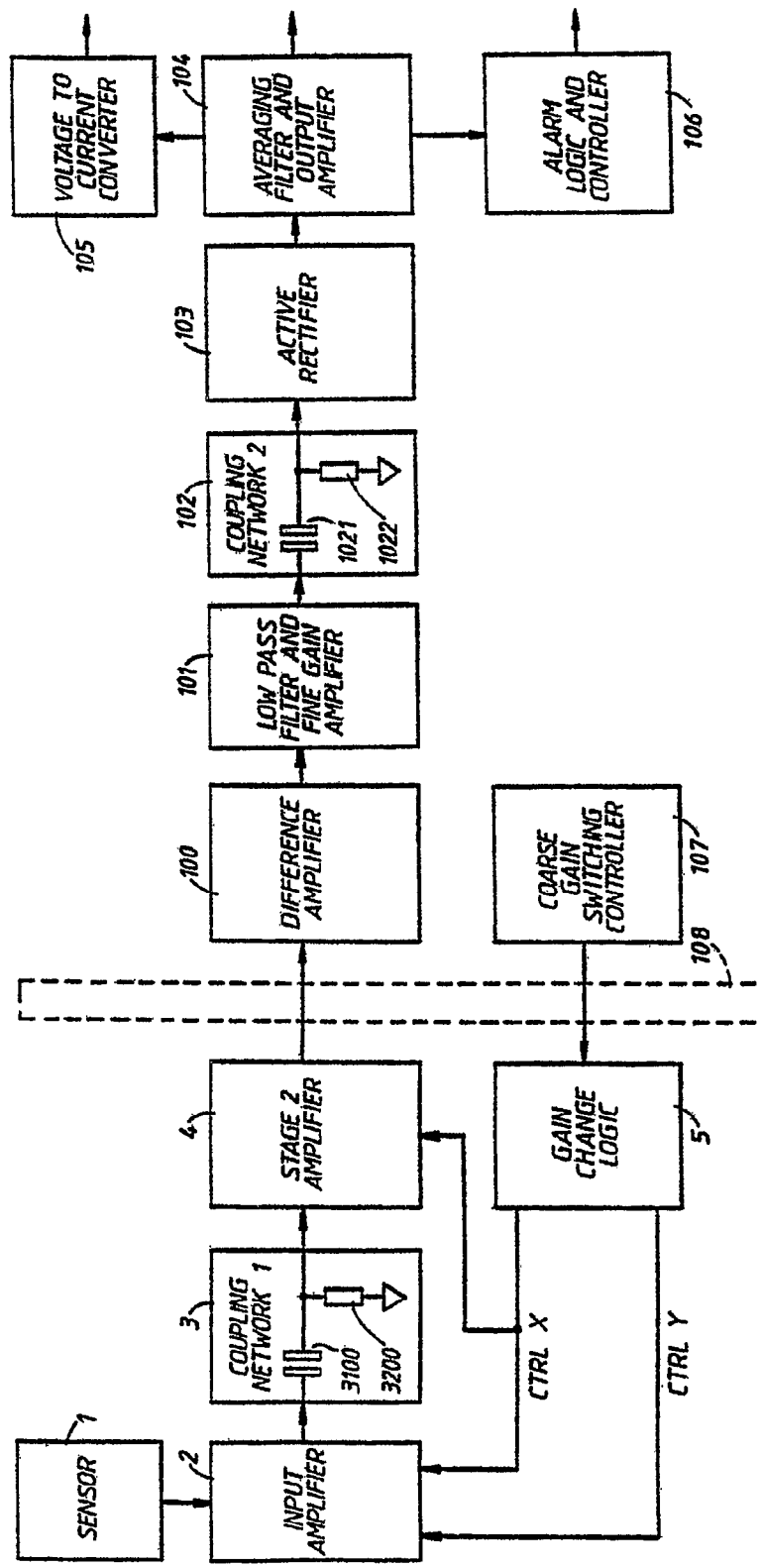
FIG. 2 is a block-diagram representation of the electrical system of the apparatus of FIG. 1.

Referring to FIG. 2 of the accompanying drawings, the electrical system of the dust flow monitoring apparatus includes an input amplifier 2, a first coupling network 3, a second stage amplifier 4, a gain-change logic circuit 5, a difference amplifier 100, a low-pass filter and fine-gain amplifier 101, a second coupling network 102, an active rectifier 103, an averaging filter and output amplifier 104, a voltage-to-current converter 105, an alarm logic and controller 106, and a coarse gain switching controller 107.

The sensor 1, the input amplifier 2, the first coupling network 3 and the second stage amplifier 4 are connected in cascade. The gain-change logic circuit 5 has a first connection connected to the input amplifier 2 and to the second stage amplifier 4, and a second connection connected only to the input amplifier 2. The coarse gain switching controller 107 is connected to the gain-change logic circuit 5.

The difference amplifier 100, the low-pass filter and fine-gain amplifier 101, the second coupling network 102, the active rectifier 103 and the averaging filter and output amplifier 104 are connected in cascade. The voltage-to-current converter 105 and the alarm logic and controller 106 are connected to the averaging filter and output amplifier 104.

The sensor 1, the input amplifier 2, the first coupling network 3, the second stage amplifier 4 and the gain-change logic circuit 5 form a sensing head which, in use, is housed in body 8 and mounted on a stack 6, the dust flow along which is being monitored.

The remainder of the electrical system is "control room" equipment and is in this embodiment located at a position remote from the sensing head. The second stage amplifier 4 of the sensing head 6 is connected to the difference amplifier 100 of the "control room" equipment by way of a connection means 108 which might include a length of cable. (In an alternative embodiment, some of those elements are in the sensing head.) The gain-change logic circuit 5 is connected to the coarse gain switching controller 107 by way of the connection means 108.

The rod 1 is a conducting rod which in this embodiment is covered by an insulating member; that may be of a ceramic or PTFE material and the insulating member extends some of the way along the conducting rod 1 towards its free end but stops short of the end. (In an alternative embodiment, the rod 1 is not insulated.)

The input amplifier 2 is a shunt-feedback current amplifier which converts its input current, which is the current supplied by the conducting rod, into an output voltage. The amplifier 2 is d.c. coupled and has switchable components providing selectable transimpedance gains of between 0.1 millivolts per picoampere and 40 millivolts per picoampere in three steps, respectively. The input amplifier 2 also includes capacitance resistance networks which set the upper frequency response at about 100 Hz.

The output signal from the input amplifier 2 passes to the first coupling network 3 which includes a series capacitor 3100 and shunt resistor 3200. The series capacitor 3100 blocks the d.c. and very low frequency signals from the input amplifier 2, the capacitor 3100 and resistor 3200 being selected to set the lower frequency response of the signal path at 1 Hz.

The signal passing through the capacitor 3100 next goes to the second stage amplifier 4 which is a d.c. coupled voltage amplifier having switchable gain-setting means for setting its gain.

The gain switching arrangements of the amplifiers 2 and 4 are so linked as to provide overall transimpedance gains of 0.2 millivolts per picoampere, 2 millivolts per picoampere, 20 millivolts per picoampere and 200 millivolts per picoampere, respectively.

The settings of the transimpedance-gain of the input amplifier 2 and the voltage gain of the second stage amplifier 4 are effected by the gain-change logic circuit 5 operating under the control of the coarse gain switching controller 107 which is controlled manually.

The selected maximum transimpedance gain of the input amplifier 2 provides a good signal-to-noise ratio for the system by ensuring that a significant proportion of the required system gain is provided at the input stage without raising significant difficulties of temperature-generated output voltage. The potential difficulty of temperature-generated output voltage is also met by limiting the lower frequency of the transmission path to 1 Hz by means of the first coupling network 3. The selection of the upper frequency limit as 10 Hz is effective to counter the effects of mechanical vibration and noise while providing a bandwidth adequate for providing accurate information on the flow rate of dust particles impinging on the sensor 1.

That is, the system bandwidth is carefully selected in order to counter a range of system effects which generate signals likely to cause errors in the final result.

Other turn-over frequencies may be used at the cost of reduced effectiveness of the system in discriminating against unwanted effects.

The bandwidth-limited output signal from the second stage amplifier 4 passes to the difference amplifier 100 where it is subjected to additional bandwidth-shaping by means of capacitor-resistor networks in order to improve the high-frequency roll off above 10 Hz. The difference amplifier 100 is a differential amplifier and has a high common-mode rejection ratio. The capacitor-resistor networks include a parallel capacitor-resistor network shunting the non-inverting input terminal of the amplifier and another parallel capacitor-resistor network connected between the inverting input terminal of the amplifier and its output terminal.

The signal next passes to the low-pass filter and fine-gain amplifier 101 where further low-pass characteristic shaping is applied by means of capacitance-resistance networks which provide a roll-off above 10 Hz; the roll-off rate is at least 12 dB/octave.

The second coupling network 102 receives the signal from the low-pass filter and fine-gain control amplifier 101. The second coupling network 102 has a series capacitor 1021 and a shunt resistor 1022 and serves to block temperature-generated signals and time-dependent d.c. signals introduced after the first coupling network 3.

The signals passing through the coupling network 102 go to the active rectifier 103 which also provides a voltage gain of 2. The signals then pass to the averaging filter and output amplifier 104 which provides a long-term average of the signals, reducing the random signal variations which particle flow provides. The averaging filter and output amplifier also provides a voltage gain of 5. (In an alternative embodiment, the signal processing is done in software.)

The averaging filter and amplifier 104 provides signals for a voltage-to-current converter 105 for further processing, as described below. The voltage-to-current converter is capable of providing a 4 to 20 mA output current swing for an input voltage swing of 0 to 10 volts. The averaging filter and amplifier 104 also provides an output of range 0 to 10 volts.

A signal from the averaging filter and output amplifier 104 is applied to the alarm logic and controller 106 which is set to trigger when a set level is exceeded. There is also an arrangement for setting the alarm logic and controller 106 to trigger when the applied signal falls below a set threshold.

Much of the electrical-interaction system of the dust flow monitoring apparatus is of a type known in the prior art, see for example U.S. Pat. No. 5,591,895, the content of which is hereby incorporated herein by reference.

Turning now to the scattered-light monitoring component of the apparatus 7, instrument 10 (FIG. 3) comprises an external housing 20 (forming part of body 6), containing a laser and a large-area photodiode (not shown) and a probe housing comprising a proximal portion 30, a medial portion 40 and a distal portion 50, which are cylindrical metal tubes, of circular cross-section. The proximal and distal housing portions are of the same diameter. The medial portion 40 joins the distal portion to the medial portion and is of a smaller diameter.

When instrument 10 is mounted in a stack, external housing 20 is positioned outside the stack wall, out of the harsh environment in which particles are flowing, whereas the distal (50), medial (40) and at least part of the proximal (30) housing portions project into the stack, the medial portion being well inside the particle flow, so as to enable reliable readings of flow rates or the like with reduced influence from the flow effects associated with the walls of the stack.

The laser produces a beam 60 which travels from external housing 20, through proximal housing portion 30, out of first aperture 35 and into scattering volume 65 (FIG. 4). Scattering volume 65 is the space, between proximal housing portion 30 and distal housing portion 50, resulting from the reduced diameter of medial portion 40.

Particle flow 67, the properties of which are to be measured by the instrument, flows through scattering volume 65. When beam 60 impinges on the particles, light is scattered at angles that depend inter alia on the size of the particles. Forward-scattered light passes into distal portion 50 through second aperture 55.

In distal portion 50, scattered light 90 falls on mirror 70 (FIG. 5). Mirror 70 is a curved mirror having a radius of curvature of 50 mm. Light scattered at angles between 4° and 8° is incident on mirror 70 and is reflected and focused by mirror 70 into an end of a waveguide 80.

Mirror 70 has a 13 mm diameter hole at its centre. Light from beam 60 that is not scattered by the particle flow (or that is scattered at less than)4° passes through that hole and is redirected into a beam dump, where it is absorbed.

Waveguide 80 is a quartz rod of 8 mm diameter. It runs from just inside the distal housing portion 50, through the interior of medial portion 40, and proximal portion 30 to the sensor in housing 20. Waveguide 80 is curved at its end 130 closest to mirror 70, so that end 130 points towards mirror 70, and can be positioned to face directly into the reflected scattered light increasing the amount of light coupled into the waveguide. For the rest of its length, waveguide 80 runs parallel to the longitudinal axis of the probe housing.

At the other end of waveguide 80, closest to the sensor, a small heat-absorbing filter is provided which reduces the amount of infrared light (which is generally undesirable in these measurements) reaching the sensor.

Waveguide 80 runs inside an elongate tube 45, which runs along the length of the probe. Part of tube 45 forms medial housing portion 40; the rest runs inside distal portion 50 and proximal portion 30. As well as being a mechanical support within the instrument and a conduit for purged air, tube 45 serves to prevent stray light and, in the medial portion, particles from impinging on waveguide 80.

Two iris outlets are provided within proximal housing portion 30. The irises are adjusted to allow most of beam 60 to pass into scattering volume 65 whilst reducing the amount of unwanted, stray light that can pass out of proximal housing portion 30.

Two air purges are provided, one adjacent to aperture 35 and one adjacent to aperture 55. The purges serve to reduce contamination of the optical surfaces of the instrument 10 by particles from the stack flow.

The sensor in housing 20 provides a current when scattered light is detected. The current signal is processed by conventional means to produce a signal indicative of particle flow in stack 6.

The scattered-light monitoring system of the dust-flow monitoring apparatus is of a type known in the prior art, see for example in the prior art, see for example the International Patent Application published under the number WO2006/082417, the content of which is hereby incorporated herein by reference. See also WO04/008117, the content of which is also hereby incorporated herein by reference.

Figure 6:
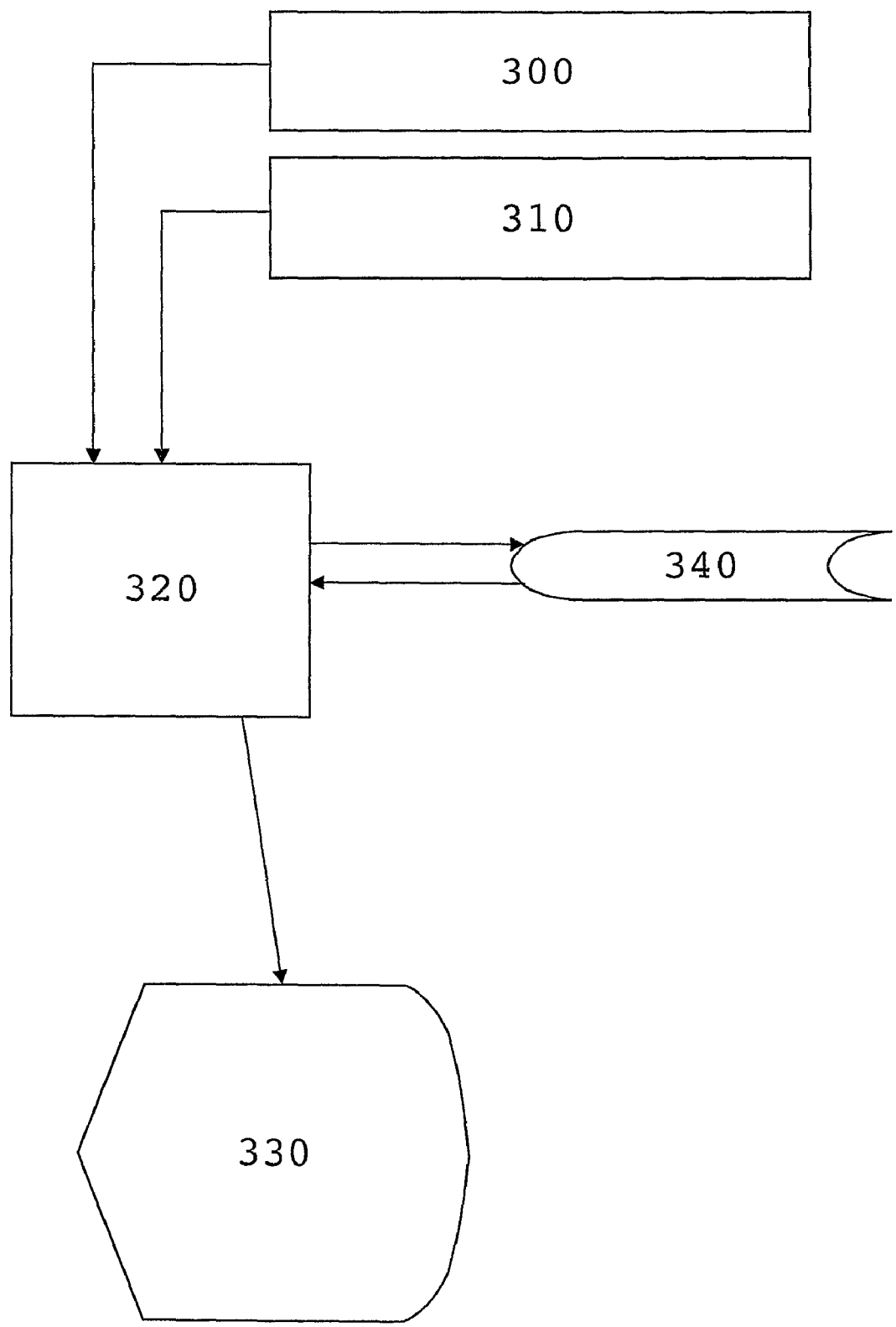
FIG. 6 is a block diagram showing the signal processing components of the apparatus of FIG. 1.

The signal from the electrical system 300 and the signal from the scattered-light system 310 are monitored by a controller 320 (FIG. 6). Controller 320 outputs a representation of particle flow in the stack 6 to display 330. Control unit 320 stores in and retrieves from a memory 340 information relating to the relative calibration of systems 300, 310.

Figure 7:
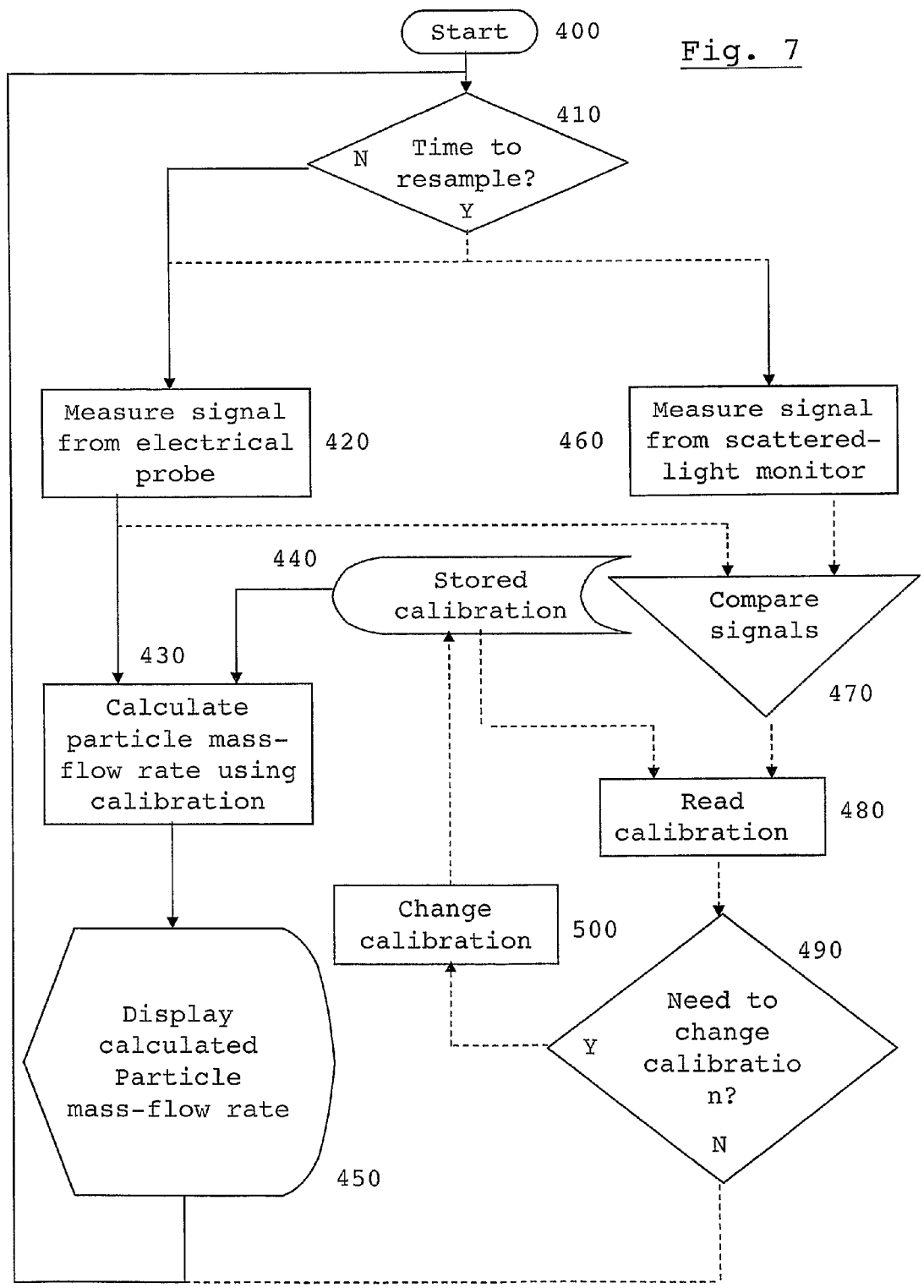
FIG. 7 is a flow chart showing how a signal representative of the particle flow is produces from the apparatus of FIG. 1.

Controller 320 includes a microprocessor programmed to run in accordance with the method illustrated in FIG. 7. In operation, electrical system 300 is run continuously, whereas scattered light system 310 is run intermittently, being run at regular intervals to provide a check of the calibration of electrical system 300.

Most of the time, the apparatus is operated according to the method illustrated by following the solid lines in FIG. 7. In the first step 420 of the electrical measurement, processor 320 obtains a signal from electrical system 300, the signal resulting from particles flowing in stack 6 interacting electrically with probe 1. Processor 320 obtains (step 440) from memory 340 pre-established calibration data which processor 320 uses to calculate (step 430) the mass-flow rate from the signal from the electrical system 300. The calculated mass-flow rate is displayed (450) to a user of display 330.

Steps 410 to 450 are repeated continuously.

At regular intervals, processor 320 determines (step 410) that it is time to resample and recalibrate electrical system 300 and so it activates scattered-light system 310. In addition to the method following the solid line in FIG. 7, which continues, as stated above, the method illustrated by following the dashed lines in FIG. 7 is now simultaneously followed.

In the first step 450 of the scattered-light measurement, controller 320 obtains a signal from scattered-light system 310, the signal resulting from particles flowing through measuring zone 65 to scatter light 90. Processor 320 compares (step 470) the signal obtained in that way with the signal simultaneously obtained from the electrical system 300 in step 420. Controller 320 also reads from memory 340 the stored calibration data.

Controller 320 then decides (step 490) on the basis of the signal comparison 470 and the stored calibration data whether the electrical system 300 is adequately calibrated, or whether it needs recalibration. If it is adequately calibrated, the apparatus reverts to electrical-only measurement, without further changes. If it needs recalibration, the controller 320 calculates the new calibration data and stores it in memory 340 (step 500). The controller then uses the newly-stored calibration data to adjust the calculated particle mass flow rate (step 430) and display it to the user (step 450), the electrical-only method then continuing as before.

Periodically, the calibration of the scattered-light monitor 310 is tested by exposing it to flowing surrogate particles, to simulate scattering from dust. The mass flow rate and other parameters of the surrogate particles are known, and so the calibration of the monitor 310 can be checked by checking that it provides readings consistent with the known values. If necessary, monitor 310 is recalibrated.

If monitor 310 is recalibrated, the above-described procedure is run in order to re-calibrate electrical-interaction monitor 300.

The electrodynamic sensing surface and light-scatter instrument may be combined on a single probe; thus, in an alternative example embodiment (FIG. 8(*a*)), light-scatter probe 610 is mounted on body 620. Probe 610 includes tube 630, which corresponds to the tube in FIG. 4 that forms medial portion 40 and can be seen in FIGS. 4 and 5 to extend along the length of probe 10. The probe also includes distal portion 640, corresponding to distal portion 50 in the embodiment of FIGS. 3 to 5. The light-scatter probe 610 functions in substantially the same way as probe 10. However, distal portion 640 acts as an electrodynamic probe, being electrically connected to signal-processing circuitry.

In a further alternative example embodiment (FIG. 8(*b*)), rod 650 is identical to rod 610 save that it is sprayed with polyetherether ketone (PEEK). Distal portion 640, which again functions as an electrodynamic probe, is extended with a further rod portion 660. That extended rod portion 660 improves the probe's electrodynamic performance by increasing the surface area which interacts electrically with flowing particles.

Whilst the present invention has been described and illustrated with reference to particular embodiments, it will be appreciated by those of ordinary skill in the art that the invention lends itself to many different variations not specifically illustrated herein. Some examples of such variations and alternatives have been described above.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims.

The invention claimed is:

1. A method of monitoring particles flowing in a stack, comprising:
   (1) monitoring a signal resulting from electrical interaction of the particles with an electrical-interaction monitor having a first calibration;
   (2) calculating from the monitored electrical-interaction signal, according to the first calibration, a value for a parameter relating to the particle flow;
   (3) monitoring a signal resulting from detection of light scattered from the particles;
   (4) comparing the electrical-interaction signal with the scattered-light signal to obtain a relative magnitude of the signals;
   (5) identifying a change in the relative magnitude of the signals;
   (6) altering the calibration of the electrical-interaction monitor in response to the change; and
   (7) calculating from the monitored electrical-interaction signal, according to the altered calibration, an altered value for the parameter relating to the particle flow, in which the signals are compared by calculating the ratio of the electrical-interaction signal to the scattered-light signal, and changes in that ratio identified.

2. A method as claimed in claim 1, in which the scattered-light signal is monitored intermittently.

* * * * *

UNITED STATES PATENT AND TRADEMARK OFFICE
CERTIFICATE OF CORRECTION

PATENT NO.       : 8,375,766 B2                                          Page 1 of 1
APPLICATION NO. : 12/520217
DATED            : February 19, 2013
INVENTOR(S)      : Rigby et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 890 days.

Signed and Sealed this
First Day of September, 2015

Michelle K. Lee
*Director of the United States Patent and Trademark Office*